United States Patent [19]

Shiramizu

[11] Patent Number: 5,522,918
[45] Date of Patent: Jun. 4, 1996

[54] APPARATUS FOR ANALYZING ORGANIC SUBSTANCE AND METHOD FOR THE SAME

[75] Inventor: Yoshimi Shiramizu, Tokyo, Japan

[73] Assignee: NEC Corporation, France

[21] Appl. No.: 356,489

[22] Filed: Dec. 15, 1994

[30] Foreign Application Priority Data

Dec. 17, 1993 [JP] Japan ..................... 5-318623

[51] Int. Cl.$^6$ ..................................... B01D 15/08
[52] U.S. Cl. ................... 95/87; 95/115; 95/143; 96/101; 96/143; 73/19.02; 73/23.27
[58] Field of Search ..................... 95/82, 87, 89, 95/90, 106, 114, 115, 141, 143; 96/101, 104, 105, 108, 143, 144, 146; 73/19.02, 23.25, 23.36, 23.37, 23.41

[56] References Cited

U.S. PATENT DOCUMENTS

| | | | |
|---|---|---|---|
| 3,769,776 | 11/1973 | Berg ............................... | 95/87 |
| 4,003,257 | 1/1977 | Fletcher et al. ............... | 95/141 X |
| 4,500,432 | 2/1985 | Poole et al. ................... | 95/82 X |
| 4,636,227 | 1/1987 | Yin et al. ...................... | 96/108 X |
| 4,684,510 | 8/1987 | Harkins ......................... | 95/137 X |
| 4,805,441 | 2/1989 | Sides et al. ................... | 95/87 X |
| 5,152,176 | 10/1992 | Bryselbout et al. ............ | 95/87 X |

FOREIGN PATENT DOCUMENTS 2-201159  8/1990  Japan .
2-262055  10/1990  Japan .

*Primary Examiner*—Robert Spitzer
*Attorney, Agent, or Firm*—Hayes, Soloway, Hennessey, Grossman & Hage

[57] ABSTRACT

A method for analyzing organic substances, includes the steps of subcooling a semiconductor substrate to a temperature at least lower than an ambient temperature, trapping volatile organic substances present in an atmosphere on the semiconductor substrate, heating the semiconductor substrate to thereby remove the volatile organic substances from the semiconductor substrate, and analyzing the volatile organic substances. This method is capable of selectively trapping to analyze only organic substances which might be adsorbed to a semiconductor device and thereby deleteriously affect the performances of the semiconductor device.

20 Claims, 8 Drawing Sheets

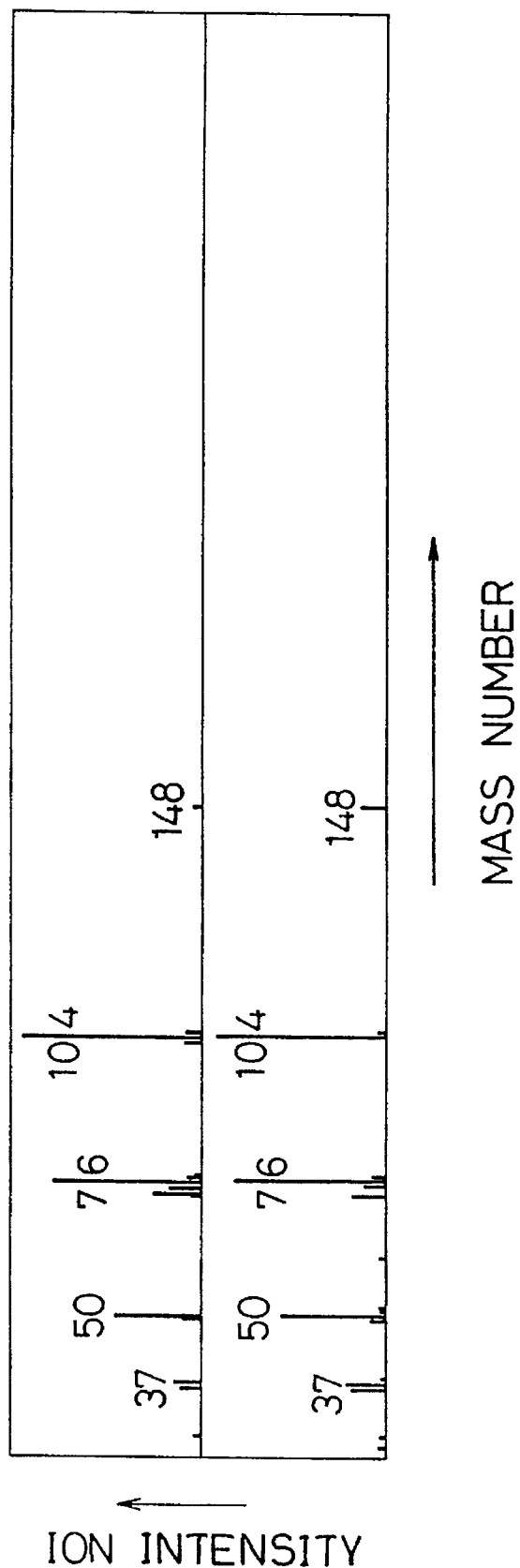

5,522,918

APPARATUS FOR ANALYZING ORGANIC SUBSTANCE AND METHOD FOR THE SAME

BACKGROUND OF THE INVENTION

1. Field of the Invention

The invention relates to an apparatus and a method for easily and accurately analyzing volatile organic substances suspending or floating in the atmosphere, and more particularly to such an apparatus and a method preferably applicable to manufacturing steps of a semiconductor device such as an analysis of organic substances involved in an air current in a clean room.

2. Description of the Related Art

An analysis of organic substances is conducted, for instance, for observing a pollution level of an atmosphere. In such an analysis, as illustrated in FIG. 1, volatile organic substances involved in an atmosphere are first trapped in an adsorbent in step 1. FIG. 2 illustrates an example of an apparatus for trapping gaseous organic substances. The apparatus comprises a pump 2, a flow meter in fluid communication with the pump 2, an adsorbent 4 contained in a duct 4a in fluid communication with the pump 2, and a support 4b for maintaining the adsorbent 4 at a certain elevation. The atmosphere 1 such as an air in a clean room is evacuated by and into the pump 2 through the adsorbent 4 for a certain period of time. The flow meter 3 regulates a flow rate of the atmosphere 1 to be constant. Thus, a certain amount of volatile organic substances can be trapped in the adsorbent 4. Then, in step 2 in FIG. 1, the adsorbent 4 is heated so that the adsorbed organic substances remove out of the adsorbent 4, and subsequently the organic substances are injected into an analyzer. Specifically, as illustrated in FIG. 3, a sample tube 5 containing therein the adsorbent 4 adsorbing volatile organic substances is heated to thereby concentrate the organic substances in trapping section 19. Then, the organic substances are separated into individual substance in a separation section 6, and then mass of each organic substance is measured in a mass measurement section 7. A data processor 8 qualitatively and quantitatively analyze the organic substances based on data supplied from the separation section 6 and mass measurement section 7. A gas chromatographic mass spectrometery is used in the analysis.

Though the above mentioned method is directed to an analysis of volatile organic substances present in an atmosphere, the method is applicable, for instance, to an analysis of organic substances present in an air current in a clean room. Japanese Unexamined Public Disclosure No. 2-201159 has suggested a method for analyzing total organic carbon present in a gas so as to upgrade the gas which is to be used in a process for manufacturing a semiconductor device. Such a gas includes, for instance, inert carrier gas such as nitrogen gas, doping gas used for forming a diffusion layer, and oxygen gas used for forming an oxide layer. The total organic carbon analyzing method includes steps of adsorbing organic carbon present in a gas into an adsorbent in cooled and concentrated state, heating the organic carbon to thereby remove from the adsorbent, and measuring organic carbon with a total organic carbon spectrometer. The Disclosure states that in accordance with the method, organic substances present in a gas to be used for manufacturing a semiconductor device can be wholly measured as carbon dioxide gas regardless of kinds of organic substances.

The above mentioned two methods for analyzing organic substances are directed to an analysis of organic substances present in a gas such as an atmosphere and a gas to be used for manufacturing a semiconductor device. On the other hand, Japanese Unexamined Public Disclosure No. 2-262055 has suggested a method for analyzing organic substances adhered to a semiconductor substrate such as a wafer during a LSI manufacturing process. The method includes the steps of extracting organic substances adhered on a wafer with $CO_2$ supercritical fluid, adsorbing the organic substances to an adsorbent in concentrated state, heating the wafer to thereby remove the organic substances out of the wafer, and analyzing the organic substances with a gas chromatography or a gas chromatographic mass spectrometery.

As illustrated in a flow chart of FIG. 1, the above mentioned three methods for analyzing organic substances commonly include the steps of trapping gaseous organic substances into an adsorbent, such as diatomaceous earth and tenax, which selectively adsorb gaseous organic substance, in concentrated state to thereby enhance sensitivity, heating the adsorbent to thereby remove the organic substances out of the adsorbent, and injecting the organic substances into an analyzer.

However, the above mentioned methods for analyzing organic substances have problems as follows.

An adsorbent, which is said to be able to selectively trap organic substance, has different trapping rates for each of organic substances, and hence it may be difficult for a certain adsorbent to trap a certain organic substance. Accordingly, it is required to prepare and use adsorbents each having different trapping rate. In addition, when an organic substance adsorbed into an adsorbent is to be removed out of the adsorbent by heating, an organic substance may be solved out from the adsorbent together with the adsorbed organic substances. Thus, it is quite difficult to analyze organic substances removed out of the adsorbent, if they were present in a quite small amount.

In a method to be applied to a semiconductor device manufacturing process, it is indispensable to identify organic substance which deleteriously affect a manufacture of a semiconductor device, among various organic substances present in an atmosphere. Thus, the above mentioned method and apparatus using a total organic carbon spectrometer is not suitable for a semiconductor device manufacturing process, because the method and apparatus do not identify organic substances and analyze organic substances which might include one deleteriously affecting a semiconductor device.

It has been recently understood that if a semiconductor substrate adsorbs organic substances present in an atmosphere, a certain kind of organic substance enormously degrades an insulative pressure proof of a silicon oxide layer. In addition, organic substances suspending or floating in an atmosphere has a low gasification temperature and a low temperature at which the organic substance is removed from a substrate. More specifically, these temperatures are equal to or lower than 400 degrees centigrade. Consequently, when a silicon oxide layer is to be grown on a semiconductor substrate on which organic substances stay as residue, the residual organic substances are decomposed and released into an atmosphere with the result that a silicon oxide layer may have a crack therein. Such a crack degrades semiconductor device properties, a yield of manufacturing semiconductor devices, and quality of semiconductor devices.

As having been described so far, with higher densification and integration of a semiconductor device, it is now necessary to measure organic substances with high sensitivity, which deleteriously affect the manufacture of semiconductor devices.

However, all of the above mentioned conventional apparatuses and methods for analyzing organic substances have problems that a certain organic substance is quite difficult to be adsorbed into a certain adsorbent, that when an adsorbent is heated for removing organic substances adsorbed therein out of the adsorbent, another organic substances are also solved out, resulting in that it is difficult to analyze a quite small amount of adsorbed organic substances, and that a total organic carbon spectrometer cannot identify organic substances which might deleteriously affect a semiconductor device.

SUMMARY OF THE INVENTION

It is an object of the present invention to provide an apparatus and a method for analyzing organic substances, which apparatus and method being capable of qualitatively and quantitatively measuring organic substances with high sensitivity, which organic substances are contained in an atmosphere in a quite small amount and deleteriously affect the manufacture of semiconductor devices.

In one aspect, the invention provides a method for analyzing organic substances, includes the steps of subcooling a semiconductor substrate to a temperature at least lower than an ambient temperature, trapping volatile organic substances present in an atmosphere on the semiconductor substrate, heating the semiconductor substrate to thereby remove the volatile organic substances from the semiconductor substrate, and analyzing the volatile organic substances.

In a preferred embodiment, the volatile organic substances present in an atmosphere are trapped in concentrated state.

In another preferred embodiment, the volatile organic substances are analyzed with a gas chromatographic mass spectrometery.

In still another preferred embodiment, the semiconductor substrate is a silicon wafer.

In yet another preferred embodiment, the semiconductor substrate is subcooled with liquid nitrogen.

In still yet another preferred embodiment, the semiconductor substrate is subcoded to a temperature in the range of $-150\pm10$ degrees centigrade.

In further preferred embodiment, the method further includes a step of wet cleaning the semiconductor substrate at first.

In further preferred embodiment, the method further includes a step of exposing the semiconductor substrate to purified dry air.

In further preferred embodiment, the step of exposing the semiconductor substrate to purified dry air is continued until the organic substances were trapped on the semiconductor substrate.

in another aspect, the invention provides an apparatus for analyzing organic substances, includes a trapping volatile organic substances present in an atmosphere on a semiconductor substrate, a subcooler for subcooling the semiconductor substrate to a temperature at least lower than an ambient temperature, a heater for heating the subcooled semiconductor substrate to a temperature at least higher than an ambient temperature, to thereby remove the volatile organic substances from the semiconductor substrate, and an analyzer for analyzing the volatile organic substances.

In a preferred embodiment, the trap contains therein the subcooler and the heater.

In another preferred embodiment, the apparatus further includes a device for keeping the semiconductor substrate in dry while the semiconductor substrate is being subcooled.

In still another preferred embodiment, the trap traps the volatile organic substances present in an atmosphere in concentrated state.

In yet another preferred embodiment, the analyzer is a gas chromatographic mass spectrometery.

In still yet another preferred embodiment, the semiconductor substrate is a silicon wafer.

In further preferred embodiment, the subcooler subcools the semiconductor substrate with liquid nitrogen.

In further preferred embodiment, the subcooler subcools the semiconductor substrate to a temperature in the range of $-150\pm10$ degrees centigrade.

In further preferred embodiment, the apparatus further includes a cleaner for wet cleaning the semiconductor substrate before trapping volatile organic substances.

In further preferred embodiment, the apparatus further includes a device for exposing the semiconductor substrate to purified dry air.

In further preferred embodiment, the exposing device exposes the semiconductor substrate to purified dry air, trapping the volatile organic substances on the semiconductor substrate.

The advantages obtained by the aforementioned present invention will be described hereinbelow.

In the apparatus and method in accordance with the invention, gaseous organic substances suspending or floating in an atmosphere are selectively trapped on a subcooled semiconductor substrate. Then, the semiconductor substrate is heated to remove the trapped organic substances from the substrate. The removed organic substances are injected into a gas chromatography mass spectrometery. Thus, organic substances present in a specific space such as a clean room can be qualitatively and quantitatively measured. Thus, the invention can selectively adsorb and analyze only organic substances which might adhere to a semiconductor substrate to thereby deleteriously affect the manufacture of semiconductor devices.

In addition, since a semiconductor substrate is subcooled, organic substances can be adsorbed in concentrated state. Hence, the invention provides the analysis of organic substances with sensitivity ten to thousand times higher than that of conventional methods.

Furthermore, since any adsorbent is not used in the apparatus and method in accordance with the invention, there is posed no problems accompanied with the use of adsorbents. Namely, it can be avoided that impurities are solved out of an adsorbent, and that a concentration efficiency of organic substances disperses.

Thus, the invention is advantageously utilized in a semiconductor manufacturing process. For instance, the invention makes it possible to identify an origin of a certain organic substance, and observe a cleanliness of a clean room atmosphere.

The above and other objects and advantageous features of the present invention will be made apparent from the following description made with reference to the accompanying drawings, in which like reference characters designate the same or similar parts throughout the drawings.

BRIEF DESCRIPTION OF THE DRAWINGS

FIG. 8 illustrates the result of mass analysis in an embodiment.

DESCRIPTION OF THE PREFERRED EMBODIMENT

A preferred embodiment in accordance with the present invention will be explained hereinbelow with reference to drawings.

Figure 1:
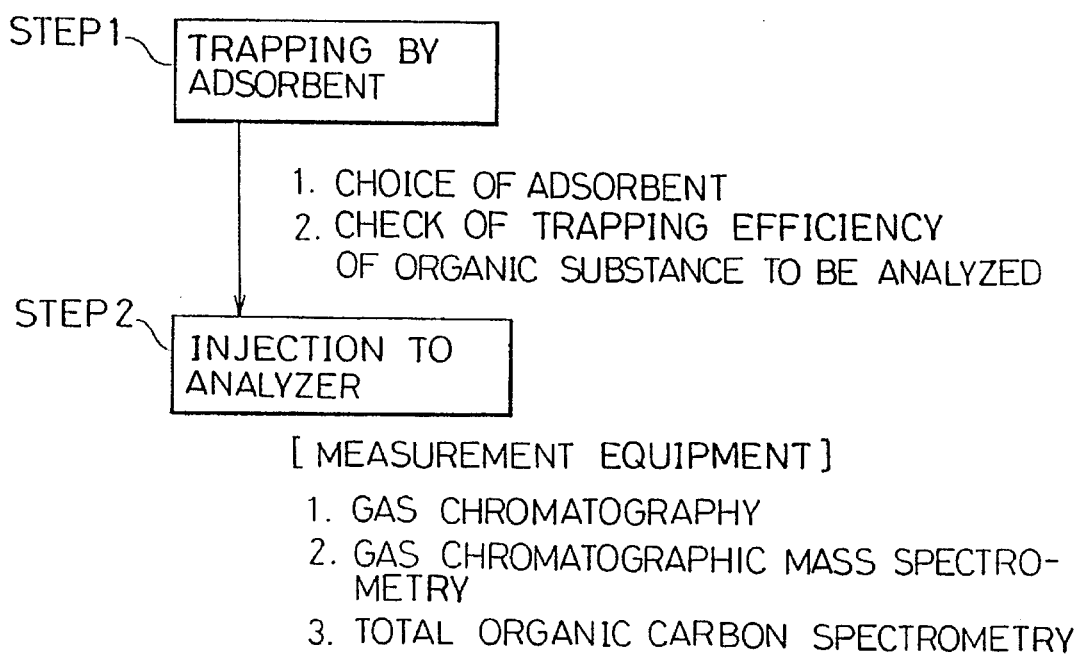
FIG. 1 is a flow chart illustrating analysis steps in accordance with a conventional method.
Figure 2:
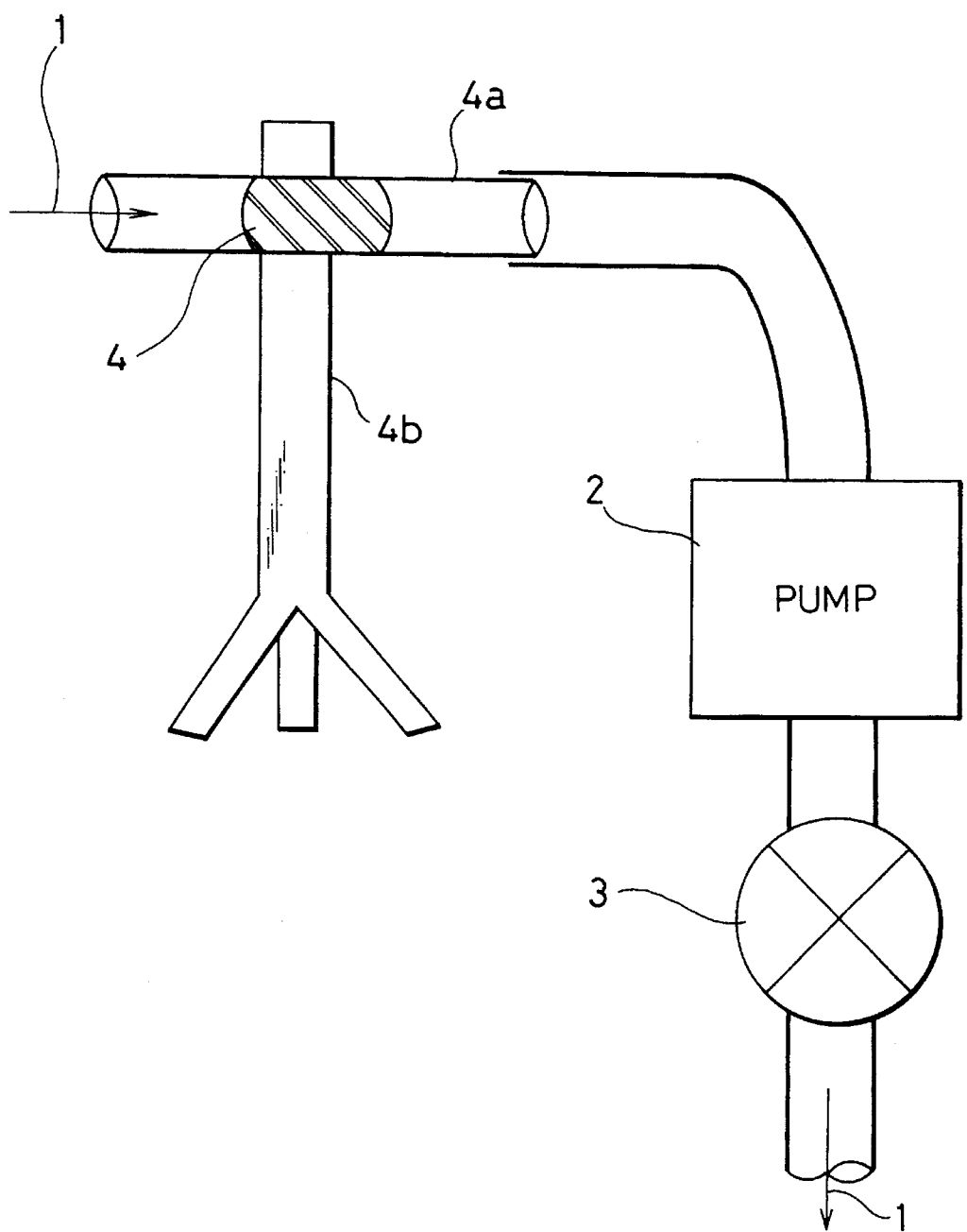
FIG. 2 is a schematic view illustrating an apparatus for trapping organic substances, used in a conventional method for analyzing organic substances.
Figure 3:
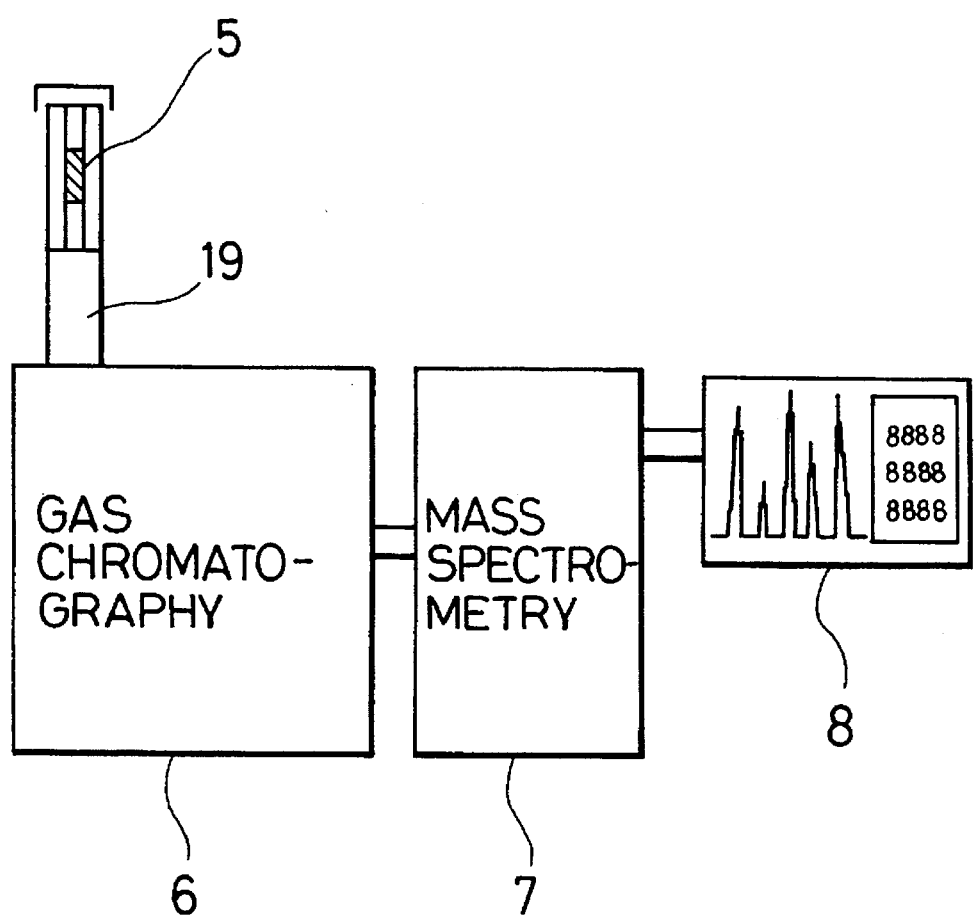
FIG. 3 is a schematic view illustrating an apparatus for analyzing organic substances, used in a conventional method for analyzing organic substances.
Figure 4:
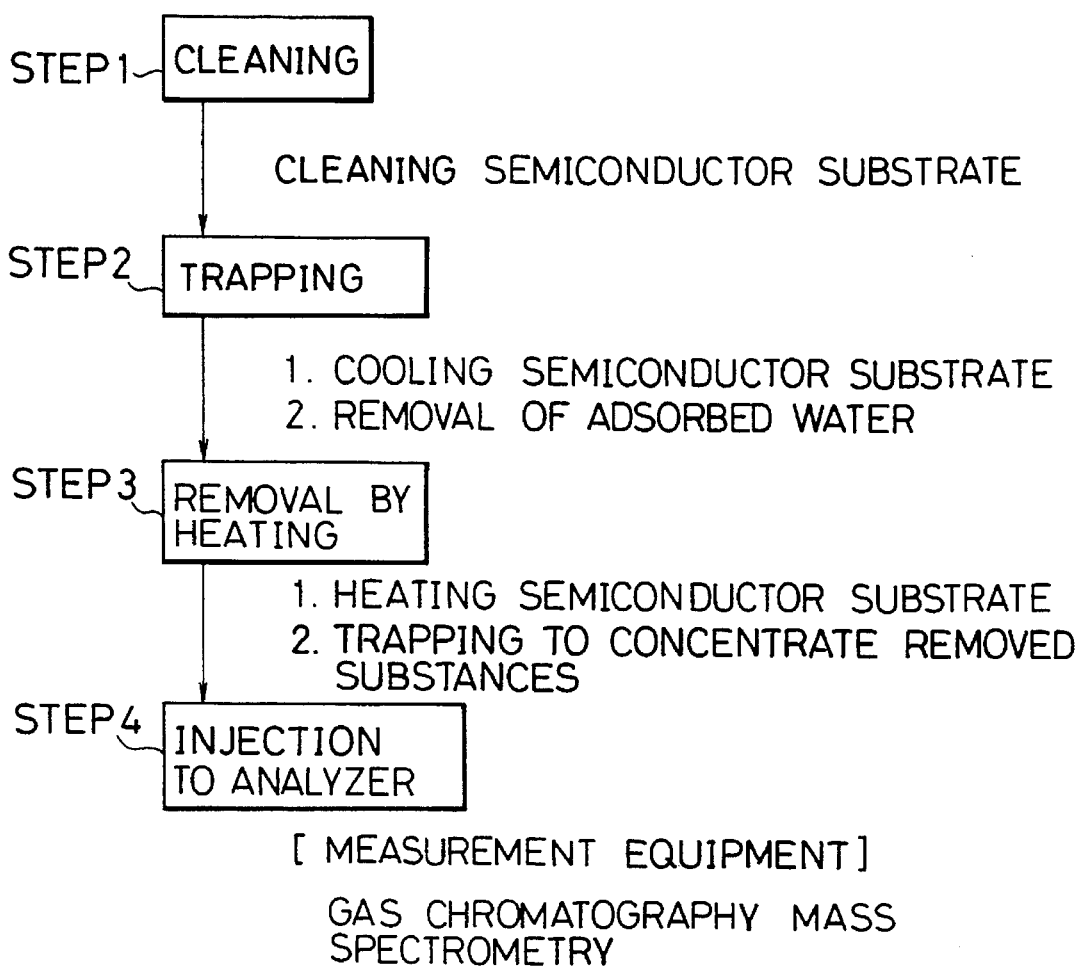
FIG. 4 is a flow chart illustrating analysis steps in accordance with the invention.
Figure 5:
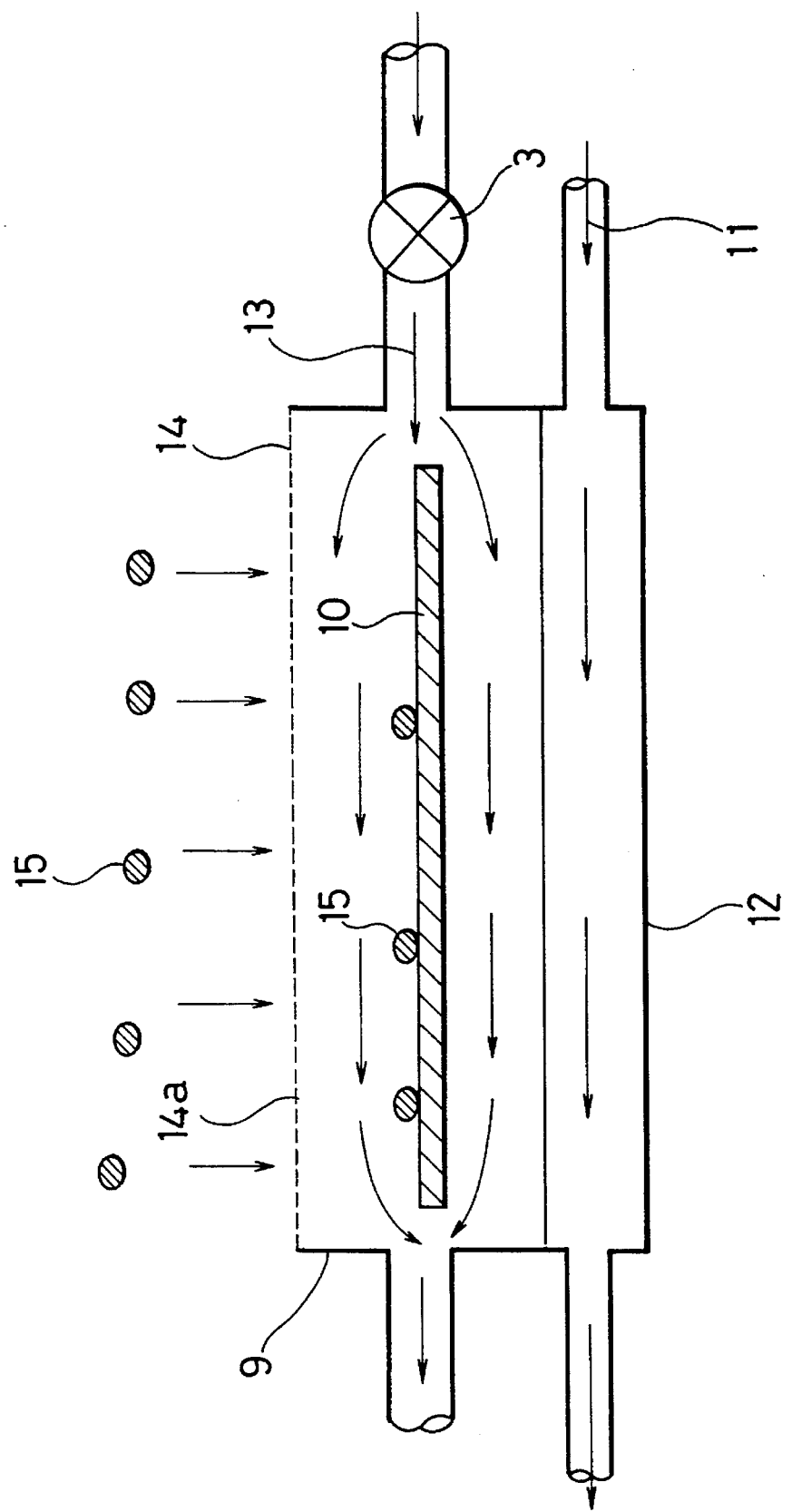
FIG. 5 is a schematic view illustrating an apparatus for trapping organic substances, used in an embodiment in accordance with the invention.

Referring to a flow chart illustrated in FIG. 4, first a semiconductor substrate such as a silicon substrate 10 is cleaned in step 1. Then, the silicon substrate 10 is placed in a chamber 9 of an organic substance trap illustrated in FIG. 5. The chamber 9 is constructed so that an air current can flow therethrough through a gas flow meter 3. Below the chamber 9 is detachably attached a cooler and heater 12 for cooling or heating the chamber 9. The chamber 9 has a cover 14 which is able to open and close, and which has a plurality of holes 14a (96 points) each having 5 mm of a diameter.

The silicon substrate 10 is cooled by the cooling and heating device 12 which is cooled with liquid nitrogen ($N_2$) 11 flowing therethrough, to a temperature in the range of $-150\pm10$ degrees centigrade. While the silicon substrate 10 is being cooled, purified dry air 13 is injected into the chamber 9 in an amount of $2\times10^{-6}$ $m^3$/sec through the gas flow meter 3 so as to avoid humidity from unnecessarily adhering to the silicon substrate 10. Then, in step 2 of FIG. 4, the cover 14 is opened for 24 hours so that gaseous organic substances 15 floating in an atmosphere are adsorbed to the silicon substrate 10.

Figure 6:
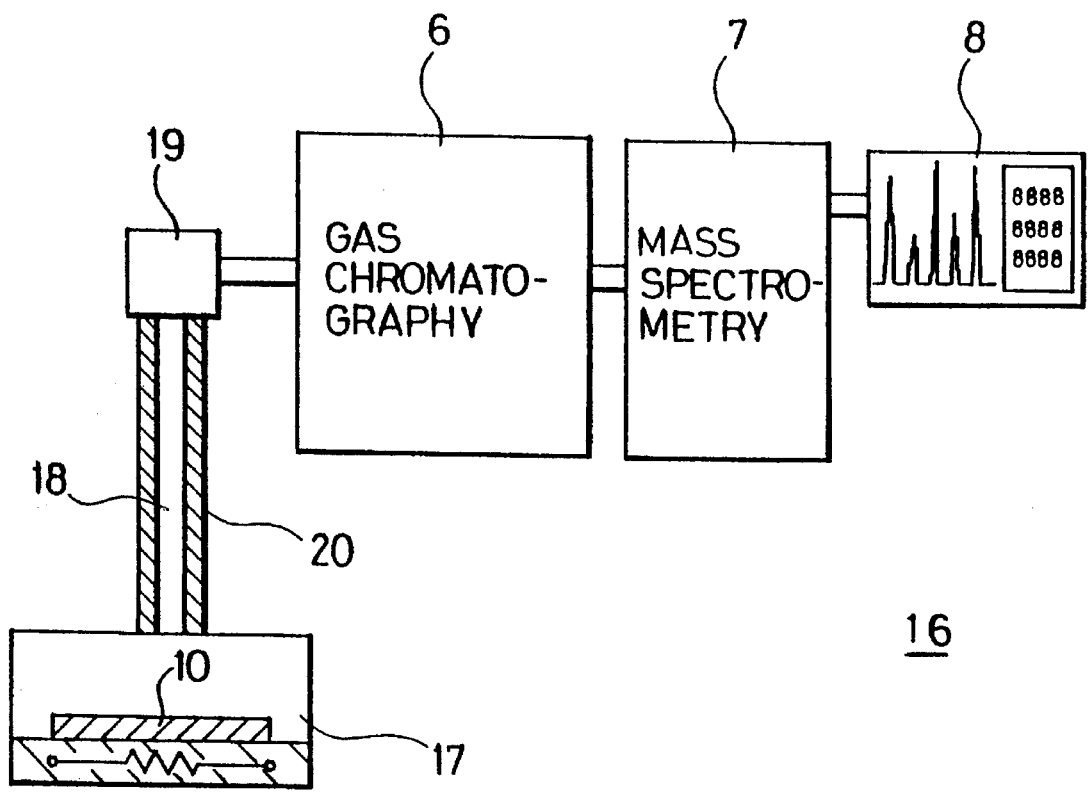
FIG. 6 is a schematic view illustrating an apparatus for analyzing organic substances, used in an embodiment in accordance with the invention.

Next, the trapped organic substances 15 are qualitatively and quantitatively analyzed with an organic substance analyzer 16 illustrated in FIG. 6. In the embodiment, the introduction of the dry air 13 into the chamber 9 is ceased after an adequate amount of gaseous organic substances 15 has been trapped on the silicon substrate 10. The silicon substrate 10 together with the cooler and heater 12 are removed from the organic substance trap, and then placed in a heating furnace 17 illustrated in FIG. 6. The placement of the silicon substrate 10 in the heater 17 is completed within 30 minutes after the silicon substrate 10 has been removed from the organic substance trap. The silicon substrate 10 is heated up to 400 degrees centigrade at which volatile organic substances adsorbed to the silicon substrate 10 are removed from the substrate. After the organic substances have been removed out of the silicon substrate 10, the removed organic substances are fed through a conduit 18 to a concentrating trap section 19 in step 3 of FIG. 4. While the organic substances are being fed through the conduit 18, the conduit 18 is kept in a high temperature with a heater 20 so as to avoid the gaseous organic substances from adhering to the inside wall of the conduit 18.

The gaseous organic substances are trapped in the concentrating section 19 for 30 minutes. Then, species of the gaseous organic substances are identified in an identification section 6, and then mass of each species is measured in a mass measuring section 7. A data processing section 8 qualitatively and quantitatively analyze the organic substances based on data transmitted from the sections 6 and 7 in step 4 of FIG. 4.

Figure 7:
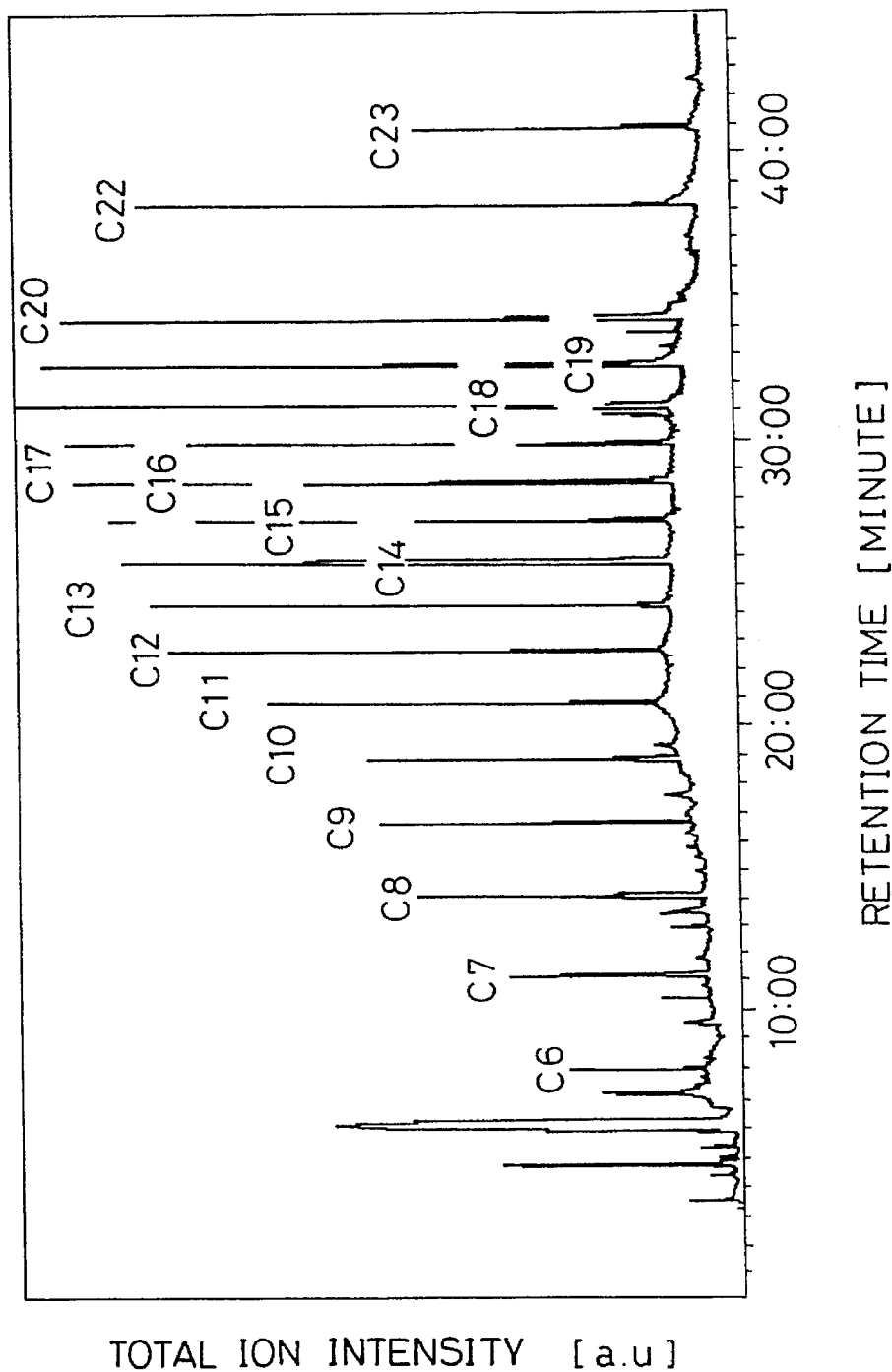
FIG. 7 illustrates the result of separation analysis in an embodiment.

FIGS. 7 and 8 show an example of an actual analysis. An ordinate of FIG. 7 represents a total ion intensity of organic substances from which it is possible to quantitatively measure organic substances on the basis of the fact that concentration of an organic substance is in proportion to a total ion strength. An abscissa of FIG. 7 represents retention time, showing that organic substances are separated into species as a function of time. In this analysis, to a surface of a silicon substrate is dropped a few drops of organic substances as a reference substance so as to separate adsorbed organic substances from the silicon substrate. Each of the dropped organic substances has known concentration, but has different carbon numbers. The known concentration is all $100\times 10^{-9}$ grams. It is understood from this example that an analysis can be achieved at $1\times10^{-9}$ grams level.

Each of the organic substances separated into species is introduced into a mass spectrometery with a certain interval. FIG. 8 shows the result of measurement of mass analysis. As shown in FIG. 8, there are obtained measurements in the range of 37 to 148. It is impossible to qualitatively analyze the organic substances only in view of these measurements. For carrying out quantitative analysis, an organic substance having the same pattern as that of FIG. 8 is retrieved among data base containing approximately 60,000 data about known organic substances. In FIG. 8, an upper stage shows the result of an actual analysis, and a lower stage shows the retrieved data. A mass analysis data shown in the lower stage of FIG. 8 is that of phthalic anhydride. Thus, one of the measured organic substances has been found to be phthalic anhydride.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method for analyzing organic substances, said method comprising the steps of:

subcooling a semiconductor substrate to a temperature at least lower than an ambient temperature;

trapping volatile organic substances present in an atmosphere on said semiconductor substrate;

heating said semiconductor substrate to thereby remove said volatile organic substances from said semiconductor substrate; and analyzing said volatile organic substances.

2. The method as recited in claim 1, wherein said volatile organic substances present in an atmosphere are trapped in concentrated state.

3. The method as recited in claim 1, wherein said volatile organic substances are analyzed with a gas chromatography mass spectrometery.

4. The method as recited in claim 1, wherein said semiconductor substrate is a silicon wafer.

5. The method as recited in claim 1, wherein said semiconductor substrate is subcooled with liquid nitrogen.

6. The method as recited in claim 5, wherein said semiconductor substrate is subcooled to a temperature in the range of −150±10 degrees centigrade.

7. The method as recited in claim 1 further comprising a step of wet cleaning said semiconductor substrate at first.

8. The method as recited in claim 1 further comprising a step of exposing said semiconductor substrate to purified dry air.

9. The method as recited in claim 8, wherein said step of exposing said semiconductor substrate to purified dry air is continued until said organic substances were trapped on said semiconductor substrate.

10. An apparatus for analyzing organic substances, said apparatus comprising:

means for trapping volatile organic substances present in an atmosphere on a semiconductor substrate;

means for subcooling said semiconductor substrate to a temperature at least lower than ambient temperature;

means for heating the subcooled semiconductor substrate to a temperature at least higher than said ambient temperature, to thereby remove said volatile organic substances from said semiconductor substrate; and means for analyzing said volatile organic substances.

11. The apparatus as recited in claim 10, wherein said trapping means contains therein said subcooling means and said heating means.

12. The apparatus as recited in claim 10 further comprising means for keeping said semiconductor substrate dry while said semiconductor substrate is being subcooled.

13. The apparatus as recited in claim 10, wherein said trapping means traps said volatile organic substances present in an atmosphere in concentrated state.

14. The apparatus as recited in claim 10, wherein said analyzing means is a gas chromatography mass spectrometery.

15. The apparatus as recited in claim 10, wherein said semiconductor substrate is a silicon wafer.

16. The apparatus as recited in claim 10, wherein said subcooling means subcools said semiconductor substrate with liquid nitrogen.

17. The apparatus as recited in claim 16, wherein said subcooling means subcools said semiconductor substrate to a temperature in the range of −150±10 degrees centigrade.

18. The apparatus as recited in claim 10 further comprising a cleaner for wet cleaning said semiconductor substrate before trapping volatile organic substances.

19. The apparatus as recited in claim 10 further comprising means for exposing said semiconductor substrate to purified dry air.

20. The apparatus as recited in claim 19, wherein said exposing means exposes said semiconductor substrate to purified dry air while said trapping means is trapping said volatile organic substances on said semiconductor substrate.

* * * * *

UNITED STATES PATENT AND TRADEMARK OFFICE
CERTIFICATE OF CORRECTION

PATENT NO. : 5,522,918
DATED : June 4, 1996
INVENTOR(S) : Yoshimi Shiramizu

It is certified that error appears in the above-indentified patent and that said Letters Patent is hereby corrected as shown below:

Title page, item [73], "Assignee: NEC Corporation, France" should read "Assignee: NEC Corporation, Japan".

Signed and Sealed this

Eighteenth Day of March, 1997

Attest:

BRUCE LEHMAN

Attesting Officer

Commissioner of Patents and Trademarks